United States Patent
Nelson et al.

(10) Patent No.: US 9,186,456 B2
(45) Date of Patent: Nov. 17, 2015

(54) FLOW SELECTOR DEVICE ALIGNMENT SYSTEM

(71) Applicant: AVENT, INC., Alpharetta, GA (US)

(72) Inventors: Christopher S. Nelson, Lake Forest, CA (US); Siddharth Desai, Ladera Ranch, CA (US)

(73) Assignee: AVENT, INC., Alpharetta, GA (US)

( * ) Notice: Subject to any disclaimer, the term of this patent is extended or adjusted under 35 U.S.C. 154(b) by 299 days.

(21) Appl. No.: 13/873,936

(22) Filed: Apr. 30, 2013

(65) Prior Publication Data

US 2014/0323987 A1    Oct. 30, 2014

(51) Int. Cl.
*A61M 5/00*    (2006.01)
*A61M 5/168*   (2006.01)

(52) U.S. Cl.
CPC ....... *A61M 5/16877* (2013.01); *A61M 5/16813* (2013.01); *A61M 2205/276* (2013.01)

(58) Field of Classification Search
CPC ............ A61M 5/168; A61M 5/16877; A61M 5/16804; A61M 5/16881
USPC ........................................................ 604/248
See application file for complete search history.

(56) References Cited

U.S. PATENT DOCUMENTS

| | | | |
|---|---|---|---|
| 3,557,747 A * | 1/1971 | Rigney et al. ................. | 116/308 |
| 5,318,515 A | 6/1994 | Wilk | |
| 7,455,072 B2 | 11/2008 | Mabry et al. | |
| D676,551 S | 2/2013 | Desai et al. | |
| 2006/0004330 A1 | 1/2006 | Carlisle et al. | |

FOREIGN PATENT DOCUMENTS

| | | |
|---|---|---|
| EP | 0 369 712 A2 | 5/1990 |
| EP | EM 002016964-0001 | 6/2012 |
| WO | WO 83/04080 A1 | 11/1983 |
| WO | WO 8809893 | * 12/1988 |
| WO | WO 2004/026373 A1 | 4/2004 |

* cited by examiner

*Primary Examiner* — Edelmira Bosques
(74) *Attorney, Agent, or Firm* — Dority & Manning, PA (57) ABSTRACT

An alignment system for accurately setting the flow rate of a flow selector device, the system includes a flow selector device having a flow rate selection mechanism rotatable between a plurality of pre-selected positions; a knob providing a grip to rotate the flow rate selection mechanism, the knob having a distal portion, a proximal portion, and at least one registering element; and a cover movable between an open position providing access to the knob and a closed position restricting access to the knob, the cover further including at least one cover element that prevents closure when the registering element is misaligned with a pre-selected position.

18 Claims, 9 Drawing Sheets

FLOW SELECTOR DEVICE ALIGNMENT SYSTEM

FIELD OF THE INVENTION

The present invention relates to devices for regulating the flow of intravenous fluids. More particularly, the present invention relates to an improved alignment system for flow selector devices used with infusion pumps.

BACKGROUND

In the medical field, therapeutic or medicinal liquids are often administered to a patient by an infusion system. There are various types of infusion systems for delivering liquids to a catheter or needle. For example, in one system the liquid is typically contained in a reservoir (a bag or a bottle) suspended above the patient, and delivered through a tube, by the force of gravity. Alternatively, the liquid may be delivered from a reservoir by an infusion pump.

It is sometimes necessary to control the flow rate at which the liquid is delivered to the patient, particularly when the liquid is to be administered continuously over an extended period of time. The flow rate may be varied depending on, for example, the specific medical treatment, type of medicinal or therapeutic agent, or the specific needs of a particular patient. Indeed, a specific patient's need or demand for a particular drug or other agent may vary over time.

A variety of devices and techniques have been devised to control the flow rate at which liquid is delivered. An exemplary device is described in U.S. Pat. No. 5,318,515 for an "Intravenous Flow Regulator Device and Associated Method", issued to Wilk on Jul. 7, 1994. That device has a freely accessible slider member for selecting a desired the flow rate. Another device is described in U.S. Pat. No. 7,455,072 for a "Device for Selectively Regulating the Flow Rate of a Fluid" to Mabry et al., issued on Nov. 25, 2004. That device has a flow rate selection mechanism that is rotatable between positions.

One difficulty with these devices is the unauthorized or unsupervised adjustments to the flow rate delivered by the device. This problem is addressed by the device described in U.S. Pat. No. 7,455,072 by utilizing an optional security cover and an optional removable key. When such a cover and removable key system is used, there is risk of error in setting the flow rate if the user fails to carefully follow directions or pay attention to the selector position with respect to indicia on the housing or the rotatable selector. For example, the orientation of the key in the device can lead a user to focus on an incorrect portion of the rotatable selector. Matching the incorrect portion of the selector with the desired (i.e., correct) selection position will result in a flow rate that may appear correct but will actually be different from the flow rate indicated by the selection position. Another complication is that a user may not properly align or register the rotatable selector with the selector position that corresponds to the desired flow rate. While the device described in U.S. Pat. No. 7,455,072 may include detent features that provide an audible or haptic response (e.g., an audible "click" or a change in rotational resistance) when the rotatable selector reaches a flow rate setting, the rotatable selector may be left slightly off position or between positions so that it is not fully aligned or registered with the flow rate setting. The result is a flow rate that may appear correct but will actually be different from the flow rate indicated by the selection position.

While the approach described in U.S. Pat. No. 7,455,072 has shown promise, improvements have been sought that would provide more precise selection of fluid flow rates, in a device that is inexpensive to manufacture, and simple and reliable to use.

Thus, there has been a need for a device that allows the selection of any of a plurality of discrete flow rates while avoiding the user error of matching the incorrect portion of the selector with the desired (i.e., correct) selection position. There has been a further need for a device in which the rotatable selector is properly aligned or registered with the selected flow rate and which remains stable over time. In addition, such a device should be easy and inexpensive to manufacture, so that it may be economically made as a disposable item, while providing a high degree of reliability in use.

SUMMARY

In response to the difficulties and problems discussed herein, the present invention provides an alignment system for accurately setting the flow rate of a flow selector device that selectively fixes the flow rate of a fluid.

The alignment system includes a flow selector device a fluid inlet, a fluid outlet and a flow rate selection mechanism that is rotated between a plurality of pre-selected positions corresponding to pre-determined flow rates.

The system also has a knob that provides a grip to rotate the flow rate selection mechanism. The knob has a body having a distal portion, a proximal portion, and at least one registering element. The knob may desirably be detachable, substantially cylindrical and uniform in diameter. The registering element may have one or more axial recesses (e.g., one axial recess or a plurality of axial recesses) defined by the knob. The portion of the knob defining the plurality of axial recesses may further define bumps configured to enhance grip. Alternatively and/or additionally, the registering element may be one or more axial ridges (e.g., one axial ridge or a plurality of axial ridges) defined by the knob.

The system includes a cover movable between an open position providing access to the knob and a closed position restricting access to the knob. In an aspect of the invention, the cover may pivot from the flow selector device between an open and closed position and the knob may nest within the cover when the cover is in the closed position.

According to the invention, the cover has at least one cover element that: (i) engages the distal portion of the knob when the registering element is misaligned with a pre-selected position preventing the cover from attaining its closed position, and (ii) engages with the registering element when the registering element is aligned with a pre-selected position allowing the cover to attain its closed position. The cover element may be at least one prong (e.g., one or more prongs) which extends away from the rest of the cover. The prong is received by at least one axial recess allowing the cover to attain its closed position. Alternatively and/or additionally, the cover element may be at least one recess (e.g., one or more recesses) that receives at least one axial ridge projecting from the knob to allow the cover to attain its closed position.

The alignment system may include a plurality of indicia (e.g., marks) corresponding to the pre-selected positions. The cover may be configured to limit visibility to one or more indicia when the cover is closed. Alternatively, the cover may be configured to limit visibility to combinations of indicia when the cover is closed.

The cover may include a window for viewing one or more indicia when the cover is closed or it may include multiple windows for viewing combinations of indicia when the cover is closed. The window or windows may be in the form of an opening or may be transparent portions of the cover or combinations thereof.

According to an aspect of the invention, the cover and/or the flow selector device may include components to enable locking the cover to the flow selector device.

The present invention also encompasses an alignment system for accurately setting the flow rate of a flow selector device that selectively fixes the flow rate of a fluid. The system includes: (a) a flow selector device including a fluid inlet, a fluid outlet and a flow rate selection mechanism that is rotated between a plurality of pre-selected positions corresponding to pre-determined flow rates; (b) a knob providing a grip to rotate the flow rate selection mechanism, the knob having a body with a distal portion, a proximal portion, and further defining a plurality of axial recesses; and (c) a cover movable between an open position providing access to the knob and a closed position restricting access to the knob, the cover further including at least one prong that: (i) engages the distal portion of the knob when an axial recess is misaligned with a pre-selected position preventing the cover from attaining its closed position, and (ii) is received by an axial recess when the knob is aligned with a pre-selected position allowing the cover to attain its closed position.

The present invention further encompasses an alignment system for accurately setting the flow rate of a flow selector device in which the alignment system includes: (a) a flow selector device including a fluid inlet, a fluid outlet and a flow rate selection mechanism that is rotated between a plurality of pre-selected positions corresponding to pre-determined flow rates; (b) a knob providing a grip to rotate the flow rate selection mechanism, the knob having a body with a distal portion, a proximal portion, and further defining at least one axial ridge; and (c) a cover movable between an open position providing access to the knob and a closed position restricting access to the knob, the cover further including a plurality of cover recesses such that: (i) the cover engages the distal portion of the knob when an axial ridge is misaligned with a pre-selected position preventing the cover from attaining its closed position, and (ii) an axial ridge of the knob is received by a cover recess when the knob is aligned with a pre-selected position allowing the cover to attain its closed position.

These and other features and advantages of the invention will become more apparent to one skilled in the art from the following description and claims when read in light of the accompanying drawings.

BRIEF DESCRIPTION OF THE DRAWINGS

The present invention will be better understood by reading the Detailed Description of the invention with reference to the accompanying drawing figures, in which like reference numerals denote similar structure and refer to like elements throughout, and in which:

FIG. 4 illustrates the underneath or bottom of the cover shown in FIG. 3.

DETAILED DESCRIPTION

In describing the various embodiments of the present invention, as illustrated in the figures and/or described herein, specific terminology is employed for the sake of clarity. The invention, however, is not intended to be limited to the specific terminology so selected, and it is to be understood that each specific element includes all technical equivalents that operate in a similar manner to accomplish similar functions.

Reference will now be made in detail to one or more embodiments, examples of which are illustrated in the drawings. It should be understood that features illustrated or described as part of one embodiment may be used with another embodiment to yield still a further embodiment. It is intended that the claims include these and other modifications and variations as coming within the scope and spirit of the disclosure.

Figure 1:
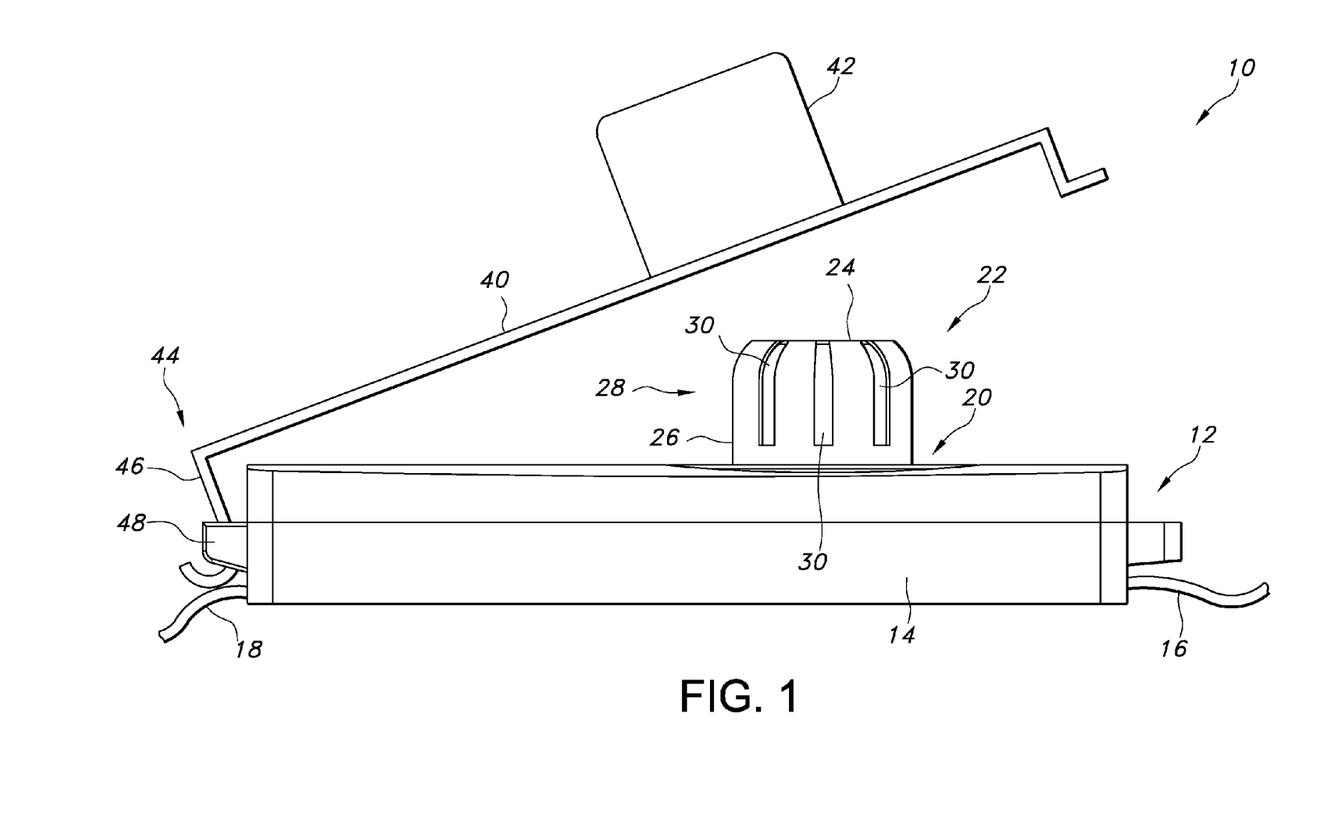
FIG. 1 is a side view illustrating an exemplary alignment system for accurately setting the flow rate of a flow selector device that selectively fixes the flow rate of a fluid.

Turning now to the drawings, FIG. 1 of the drawings is a side view illustrating an exemplary alignment system 10 for accurately setting the flow rate of a flow selector device 12 that selectively fixes or regulates the flow rate of a fluid.

The alignment system 10 includes a flow selector device 12 having a housing 14, a fluid inlet 16, a fluid outlet 18 and a flow rate selection mechanism 20 that is rotated between a plurality of pre-selected positions corresponding to pre-determined flow rates. The pre-selected positions may be identified by indicia, grooves, marks or the like on the housing or the flow selector device.

The system has a knob 22 that provides a grip to rotate the flow rate selection mechanism 20. The knob has a body having a distal portion 24, a proximal portion 26, and at least one registering element 28. The knob 22 may desirably be detachable, substantially cylindrical and uniform in diameter. The registering element 28 may be one or more axial recesses 30 (e.g., one axial recess or a plurality of axial recesses) defined by the knob.

Figure 13:
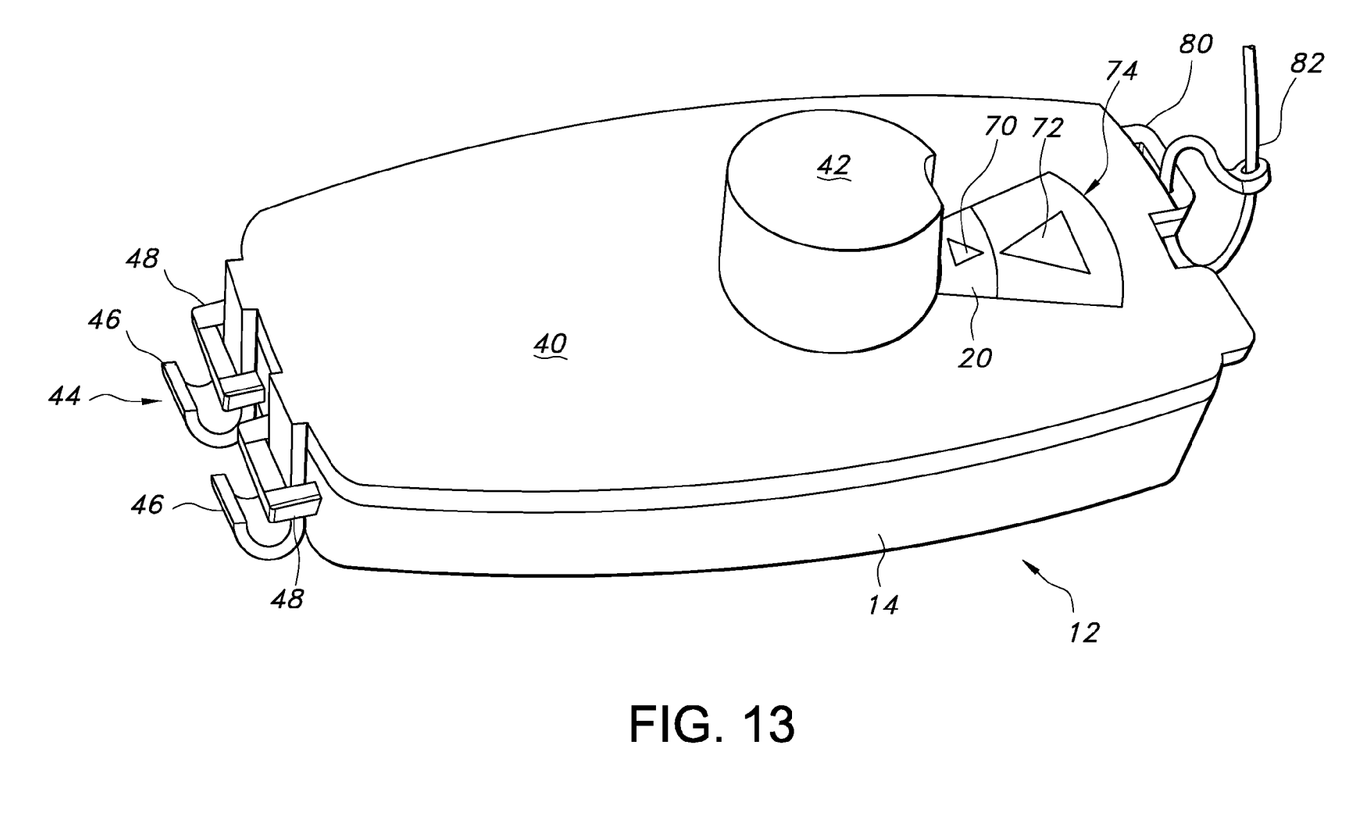
FIG. 13 is a perspective view illustrating an exemplary alignment system showing the flow selector device and its housing along with the cover in a closed position.

The system includes a cover 40. The cover 40 is movable between an open position illustrated in FIG. 1 providing access to the knob 22 and a closed position illustrated in FIG. 13 restricting access to the knob 22. The cover 40 may pivot from the flow selector device 12 (e.g., from its housing 14) between the open and closed positions. FIGS. 1 and 13 illustrate the cover 40 extending the length of the flow selector device 12—that is, the length of the housing 14 of the flow selector device 12. It is contemplated that the cover 40 may shield or conceal only a portion of the flow selector device 12. For example, the cover 40 may shield or conceal only the flow rate selection mechanism 20 of the flow rate selector device 12.

The cover 40 desirably has a portion 42 that receives the knob 22. That is, the knob 22 desirably nests within a portion 42 of the cover 40 when the cover is in the closed position. Alternatively and/or additionally, the cover 40 may have a cut-out portion (not shown) that receives the knob 22 such that the knob extends through the cover 40 rather than having the cover 40 include a portion 42 that receives the knob 22.

The cover 40 may pivot from the housing 14 of the flow selector device 12 from a hinge system 44 having cover components 46 and housing components 48. The hinge system 44 may involve a pin, living hinge, interlocking tabs, etc. It is contemplated that the hinge system 44 may be located at other portions of the housing 14 of the flow selector device 12. Such a configuration may be utilized if the cover 40 is intended to shield only a portion of the flow selector device 12. For example, the cover 40 may shield or conceal only the flow rate selection mechanism 20 of the flow rate selector device 12.

Figure 2:
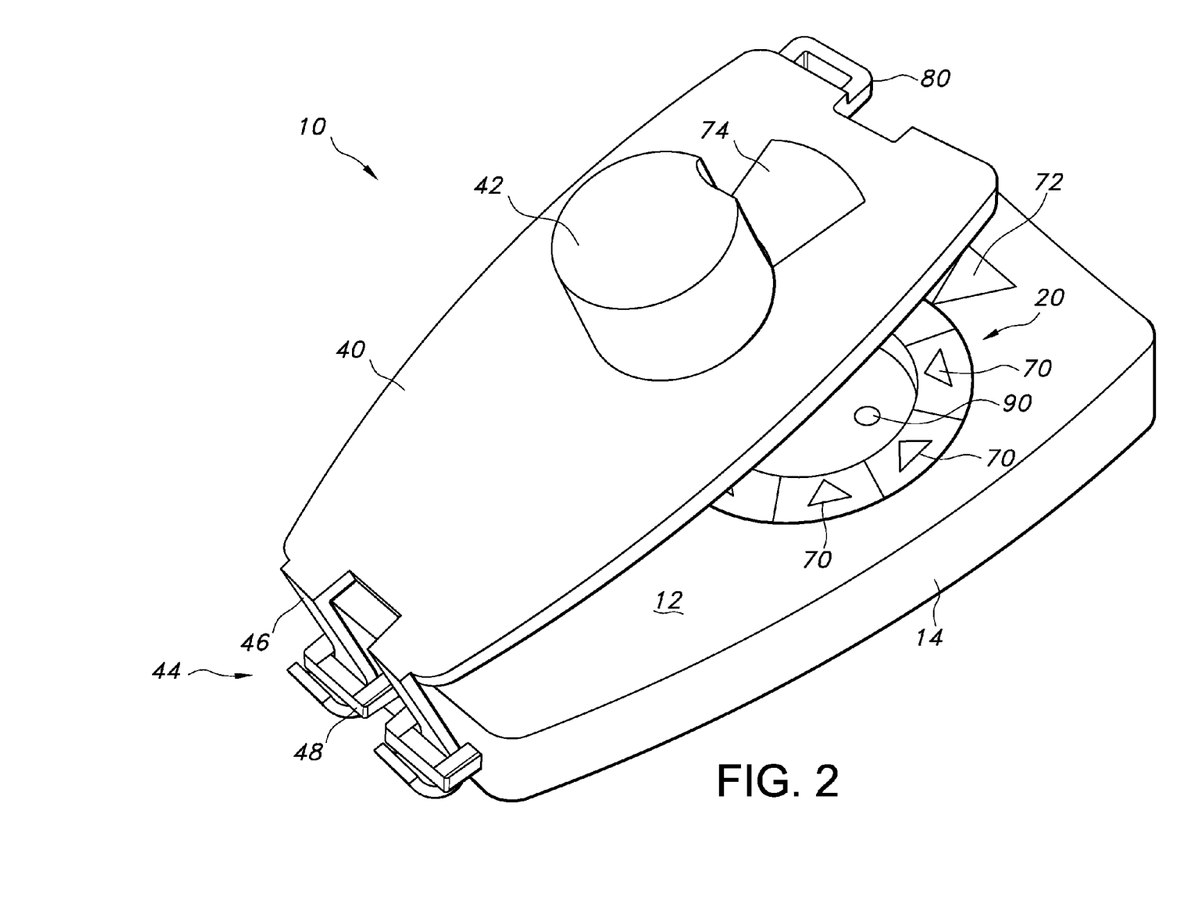
FIG. 2 is perspective view illustrating an exemplary alignment system of FIG. 1 showing the flow selector device and its housing along with the cover in an open position.
Figure 3:
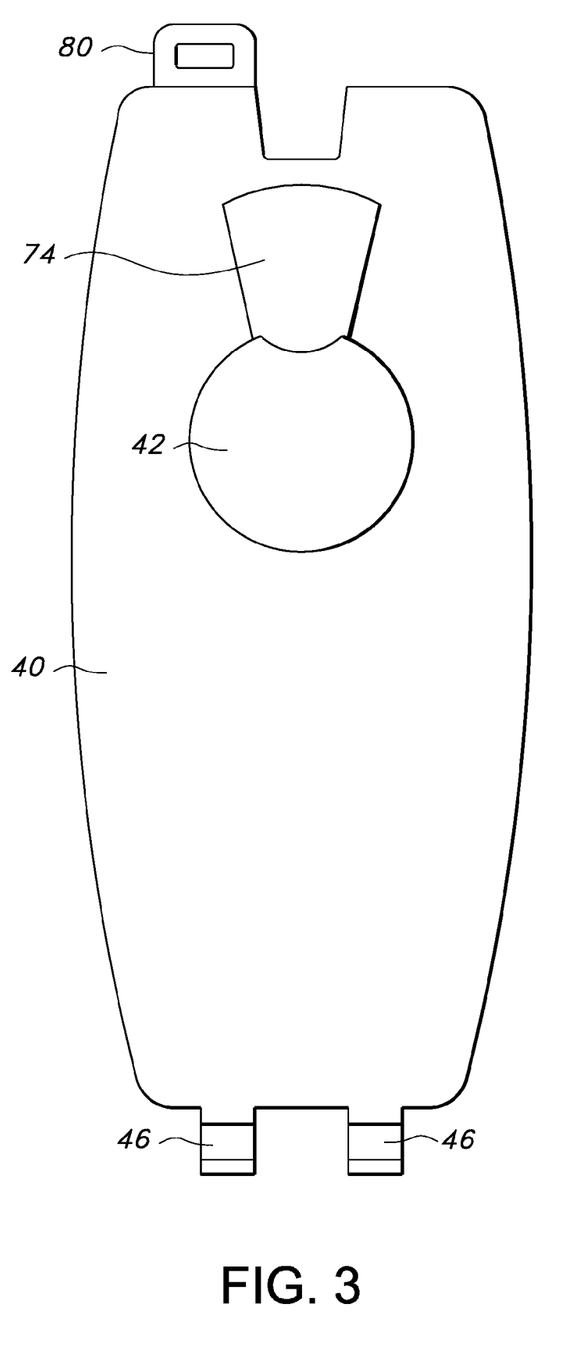
FIG. 3 is a top view of an exemplary cover detached from the housing of the flow selector device.

FIG. 2 is a perspective view illustrating an exemplary alignment system 10 and showing the flow selector device 12 and its housing 14 along with the cover 40 in an open position. The cover 40 may desirably pivot through a 180 degree range and may be detachable. FIG. 3 is a top view of an exemplary cover 40 detached from the housing 14.

Figure 4:
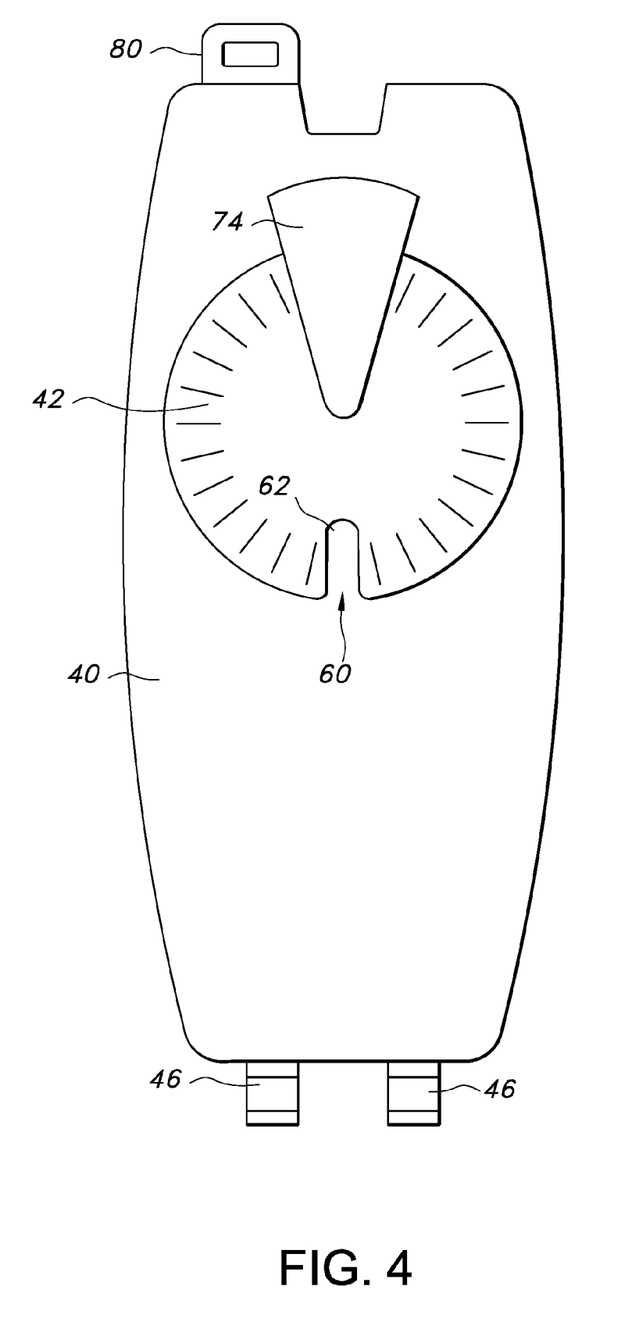
FIG. 4 is a bottom view of an exemplary cover. That is.

Referring now to FIG. 4, there is shown a bottom view of an exemplary cover 40. That is, FIG. 4 illustrates the underneath or bottom of the cover shown in FIG. 3. In this view, it can be seen that the cover 40 has at least one cover element 60. The cover element 60 is located in the cover portion 42 that receives the knob 22. The cover element may be in the form of a prong, tab or similar feature 62 that is configured to engage with a registering element 28. If the cover 40 is configured to have a cut-out portion (not shown) that receives the knob 22 such that the knob extends through the cover 40 rather than having the cover 40 include a portion 42 that receives the knob 22, the one or more cover elements 60 such as one or more tabs or prongs 62 should be robust enough to engage with one or more register element 28 such as an axial recess 30 to effectively lock the knob 22 in place so it cannot be rotated while the cover is in the closed position to prevent a patient from altering the flow rate of the flow rate selector device 12.

Figure 5A:
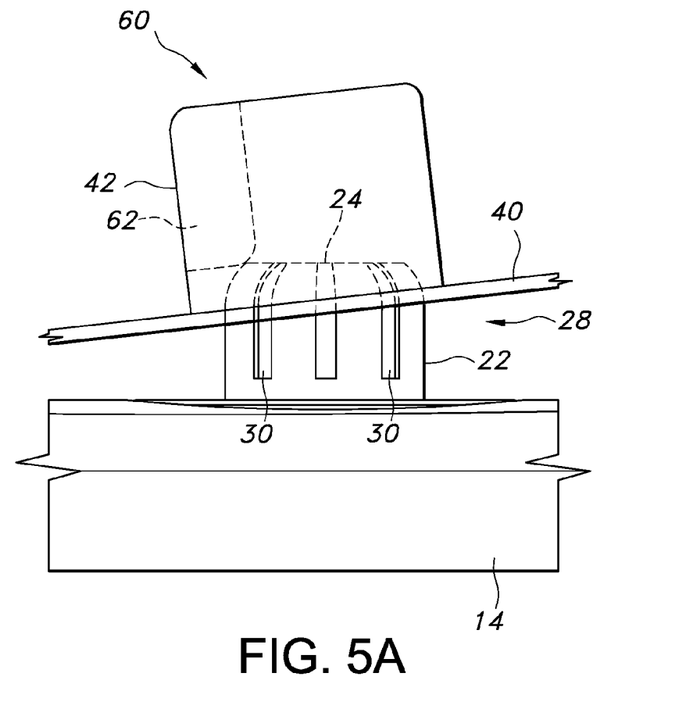
FIG. 5A is a side partial cross-sectional view illustrating a detail of an exemplary alignment system in which the cover element engages the distal portion of the knob preventing the cover from closing.
Figure 5B:
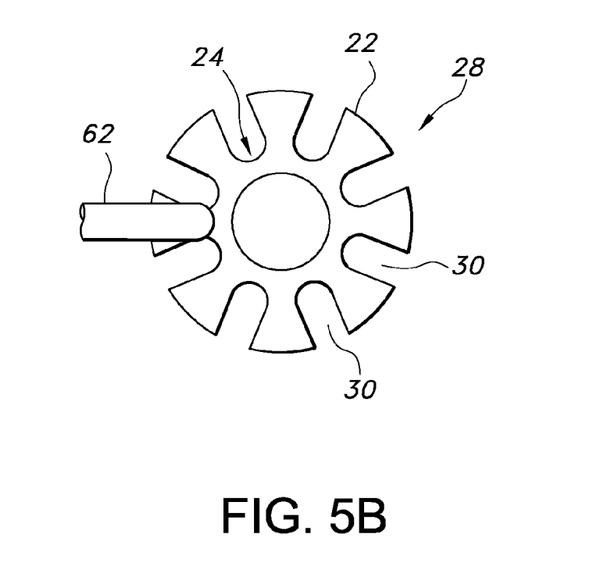
FIG. 5B is a top view illustrating a detail of an exemplary alignment system in which the cover element engages the distal portion of the knob preventing the cover from closing.

Referring now to FIG. 5A, there is shown a partial side view of an exemplary alignment system 10 and showing portions of the housing 14 along with the cover 40. In this view, the cover element 60 (which may be in the form of one or more prongs 62) engages the distal portion 24 of the knob 22 when a corresponding registering element 28 is misaligned with a pre-selected position. This prevents the cover 40 from closing properly and gives a clear and easily recognizable signal to a user or health care provider that the knob is not properly aligned or registered with a pre-selected position corresponding to pre-determined flow rate. FIG. 5B is a top view illustrating the cover element in the form of a prong 62 engaging the distal portion 24 of the knob 22 preventing the cover from closing. As can be seen, the prong 62 contacts the distal portion of the knob in the regions between the registering elements 28 in the form of axial recesses 30. The alignment system accurately sets the flow rate of the flow selector device 12 because it avoids the undesirable result of the registering element being not properly aligned or registered with a pre-selected position such that the rotatable selector is off position or between positions and not fully aligned or registered with the flow rate setting. The alignment system of the present invention avoids the result of a flow rate that may appear correct but is different from the flow rate indicated by the selection position.

Figure 6A:
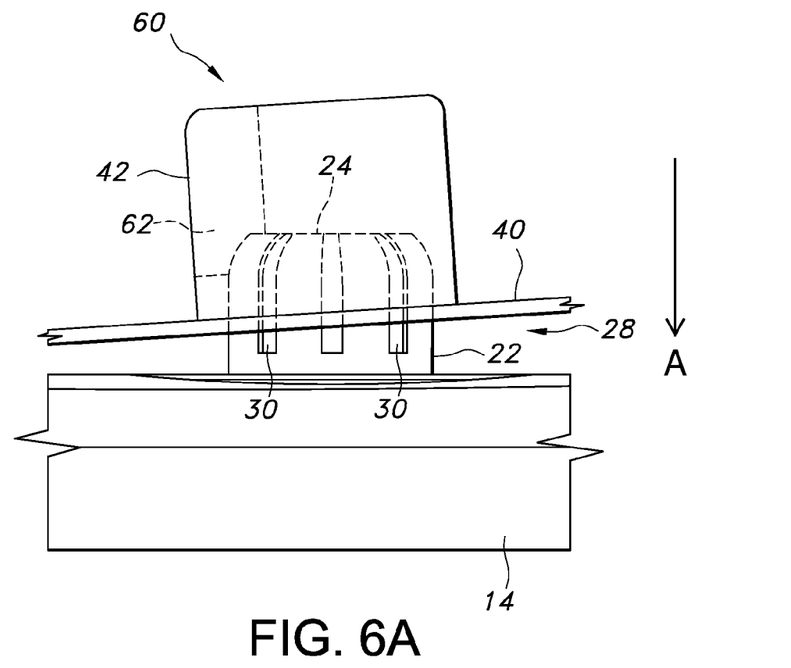
FIG. 6A is a side partial cross-sectional view illustrating a detail of an exemplary alignment system in which the cover element engages a registering element when the registering element is aligned with a pre-selected position allowing the cover to attain its closed position.
Figure 6B:
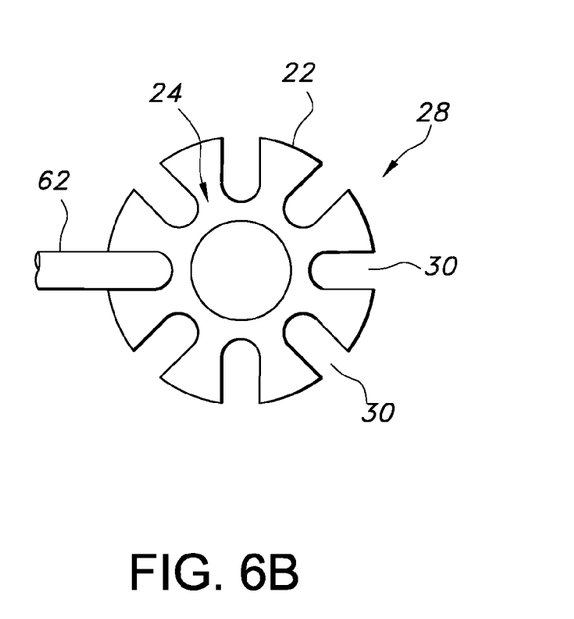
FIG. 6B is a top view illustrating a detail of an exemplary alignment system in which the cover element engages a registering element when the registering element is aligned with a pre-selected position allowing the cover to attain its closed position.

Referring now to FIG. 6A, there is shown another side view of an exemplary alignment system 10 and showing the housing 14 along with the cover 40. In this view, the cover element 60 (which may be in the form of one or more prongs 62) is able to proceed past the distal portion 24 of the knob 22 to engage with the knob register element 28 when the registering element is aligned with a pre-selected position allowing the cover 40 to attain its closed position as it travels in the direction of the arrow "A." As illustrated in FIG. 6A, the registering element 28 may be in the form of one or more axial recesses 30 and the cover element 60 may be in the form of at least one prong 62 (e.g., one or more prongs) that is received by the at least one axial recess 30 allowing the cover to attain its closed position. FIG. 6B is a top view the cover element in the form of a prong 62 engaging a registering element 28 in the form of axial recesses 30 when the registering element 28 is aligned with a pre-selected position allowing the cover to attain its closed position.

Figure 7:
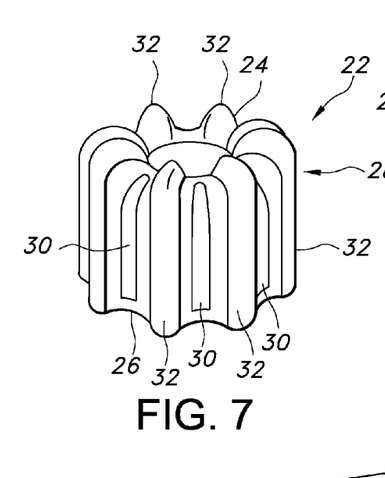
FIG. 7 is a perspective view illustrating a detail of an exemplary alignment system in which a portion of the knob may further define bumps to enhance grip of the knob.
Figure 8:
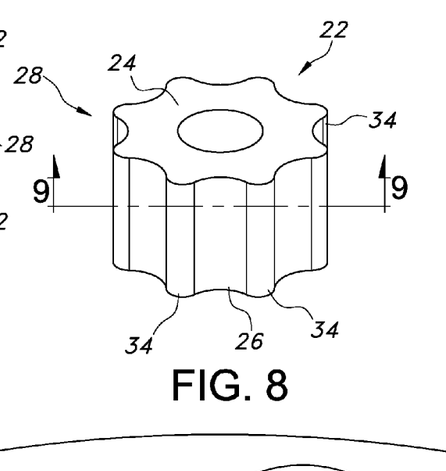
FIG. 8 is a perspective view illustrating a detail of an exemplary alignment system in which the registering element is in the form of a plurality of axial ridges.
Figure 9:
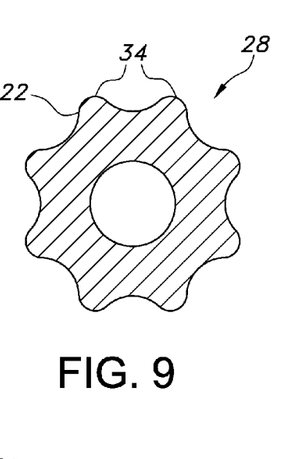
FIG. 9 is a cross sectional view taken along line "9-9" of FIG. 8.

Referring now to FIG. 7, there is illustrated a perspective view of a variation of the knob 22. As can be seen, the portion of the knob 22 defining the plurality of axial recesses 30 may further define bumps 32 configured to enhance grip of the knob 22. It is contemplated that the registering element 28 may take on other forms. As a non-limiting example and referring now to FIGS. 8 and 9, the registering element 28 may alternatively and/or additionally be one or more axial ridges 34 (e.g., one axial ridge or a plurality of axial ridges) defined by the knob 22. FIG. 8 is a perspective view of an exemplary knob 22 illustrating the registering element 28 in the form of a plurality of axial ridges 34. FIG. 9 is a cross sectional view taken along line "9-9" of FIG. 8. The axial ridges 34 and the regions between (i.e., separating) the axial ridges 34 may provide a shallow profile or a deep profile—or even variations of profiles on a single knob.

Figure 10:
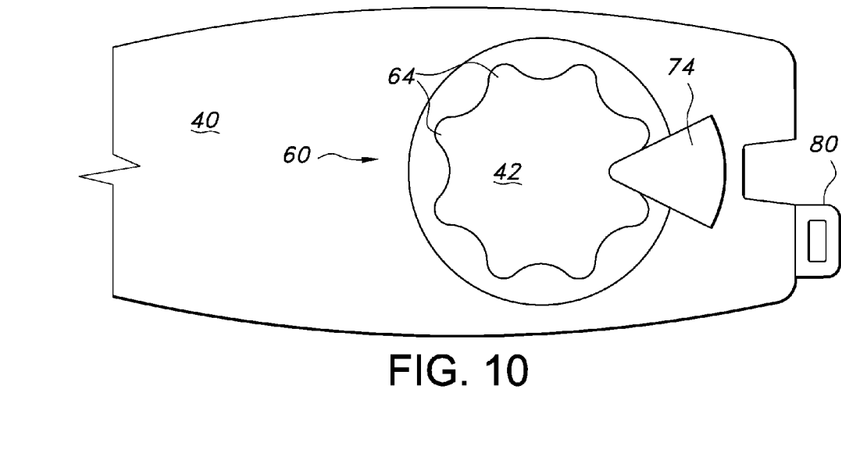
FIG. 10 is a bottom view of an exemplary cover having at least one cover element located in the cover portion that is configured to receive the registering elements as illustrated in FIGS. 8 and 9.

Referring now to FIG. 10, there is shown there is shown a bottom view of an exemplary cover 40 having at least one cover element 60 located in the cover portion 42 that is configured to receive a knob 22 containing the registering elements 28 as illustrated in FIGS. 8 and 9. As can be seen in FIG. 10, the cover 40 includes a cover element 60 that is configured to be in the form of at least one recess 64 (e.g., one or more recesses) that receives at least one axial ridge 34 on a knob 22 allowing the cover to attain its closed position.

Figures 11, 12:
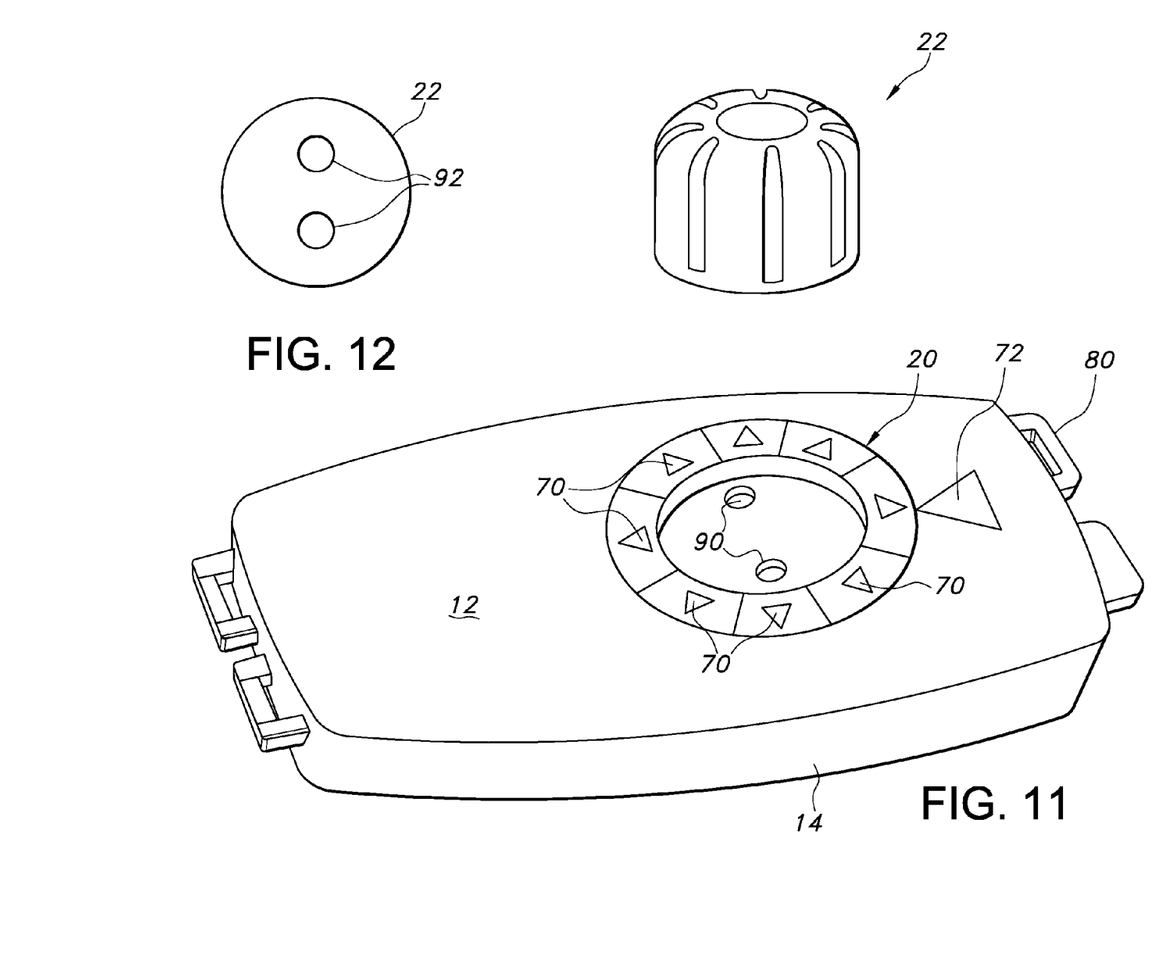
FIG. 11 is an exploded perspective view of a portion of an exemplary alignment system showing the flow selector device and its housing and a detachable knob.
FIG. 12 is a bottom view of an exemplary knob illustrating a detail of the knob.

Referring now to FIG. 11, there is illustrated an exploded perspective view of a portion of the alignment system 10 showing the flow selector device 12 and its housing 14 and a detachable knob 22. As can be seen in the illustration, the knob 22 mates with the flow rate selection mechanism 20. The flow rate selection mechanism 20 has indentations or recesses 90 that receive projections 92 from the knob 22. These projections can be seen in FIG. 12 which is a bottom view of the knob 22 illustrating the projections 92. It is contemplated that the relationship may be reversed such that the flow rate selection mechanism 20 has projections and the base or bottom of the knob 22 has indentations or recesses that receive the projections from the flow rate selection mechanism. Of course, it is contemplated that other types of detachable connections may be utilized. For example, mechanical snaps, magnets, mechanical hook and loop connections, low tack adhesives or the like.

Referring again to FIG. 11, the alignment system may include a plurality of indicia 70 (e.g., marks, decals, grooves, or the like) corresponding to the pre-selected positions of the flow rate selection mechanism 20 as well as a reference mark, point or indicia 72. The cover 40 (as shown at, for example, in FIG. 3) may be configured to limit visibility to one or more indicia (e.g., 70, 72) when the cover 40 is closed. Alternatively, the cover may be configured to limit visibility to combinations of indicia when the cover is closed. The cover 40 may include a window (e.g., a transparent plastic or glass window or the cover may define a window opening—either of which may be designated as 74) for viewing one or more indicia when the cover is closed. Alternatively and/or additionally, the cover may include multiple windows or openings for viewing combinations of indicia when the cover is closed.

According to an aspect of the invention, the cover and/or the housing may include one or more lock components 80 to enable locking the cover to the housing. These components may be tabs on each of the cover 40 and housing 14. Each tab may define an opening. When the cover is in the closed position, the tabs and their respective openings may overlap as illustrated in FIG. 13. A locking tie 82 may pass through the overlapped openings and cinched to secure the cover and housing in a closed position (shown partially cinched in FIG. 13). In this closed and locked position, the cover element 60 engages the registering element 28 so the flow rate selection mechanism 20 is also locked in position.

The present invention also encompasses an alignment system 10 for a flow selector device 12 that selectively regulates the flow rate of a fluid. The system includes: (a) a flow selector device 12 including a housing 14, a fluid inlet 16, a fluid outlet 18 and a flow rate selection mechanism 20 that is rotated between a plurality of pre-selected positions corresponding to pre-determined flow rates; (b) a knob 22 providing a grip to rotate the flow rate selection mechanism 20, the knob 22 having a body with a distal portion 24, a proximal portion 26, and further defining a plurality of axial recesses 30; and (c) a cover 40 movable between an open position providing access to the knob 22 and a closed position denying access to the knob 22, the cover 40 further including at least one prong 62 that: (i) engages the distal portion 24 of the knob 22 when an axial recess 30 is misaligned with a pre-selected position preventing the cover 40 from attaining its closed position, and (ii) is received by an axial recess 30 when the knob 22 is aligned with a pre-selected position allowing the cover 40 to attain its closed position.

The present invention further encompasses an alignment system 10 for a flow selector device 12 in which the alignment system includes: (a) a flow selector device 12 including a housing 14, a fluid inlet 16, a fluid outlet 18 and a flow rate selection mechanism 20 that is rotated between a plurality of pre-selected positions corresponding to pre-determined flow rates; (b) a knob 22 providing a grip to rotate the flow rate selection mechanism 20, the knob 22 having a body with a distal portion 24, a proximal portion 26, and further defining at least one axial ridge 34; and (c) a cover 40 movable between an open position providing access to the knob 22 and a closed position denying access to the knob 22, the cover 40 further including a plurality of cover recesses 64 such that: (i) the cover 40 engages the distal portion 24 of the knob when an axial ridge 34 is misaligned with a pre-selected position preventing the cover 40 from attaining its closed position, and (ii) an axial ridge 34 of the knob 22 is received by a cover recess 64 when the knob 22 is aligned with a pre-selected position allowing the cover 40 to attain its closed position.

While the present invention has been described in connection with certain preferred embodiments it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

We claim:

1. An alignment system for accurately setting the flow rate of a flow selector device that selectively fixes the flow rate of a fluid; the system comprising:
   a flow selector device including a fluid inlet, a fluid outlet and a flow rate selection mechanism that is rotated between a plurality of pre-selected positions corresponding to pre-determined flow rates;
   a knob providing a grip to rotate the flow rate selection mechanism, the knob comprising a body having a distal portion, a proximal portion, and at least one registering element;
   a cover movable between an open position providing access to the knob and a closed position restricting access to the knob, the cover further including at least one cover element that: (i) engages the distal portion of the knob when the registering element is misaligned with a pre-selected position preventing the cover from attaining its closed position, and (ii) engages with the registering element when the registering element is aligned with a pre-selected position allowing the cover to attain its closed position,
   wherein the knob is positioned between the flow rate selection mechanism and the cover.

2. The alignment system of claim 1, further comprising a plurality of indicia corresponding to the pre-selected positions and wherein the cover limits visibility to a single indicia when the cover is closed.

3. The alignment system of claim 2, wherein the cover includes a window for viewing the single indicia.

4. The alignment system of claim 1, wherein the at least one registering element is a plurality of axial recesses defined by the knob.

5. The alignment system of claim 4, wherein the cover element is at least one prong that is received by at least one axial recess allowing the cover to attain its closed position.

6. The alignment system of claim 4, wherein the knob is detachable, substantially cylindrical and uniform in diameter and the portion of the knob defining the plurality of axial recesses further define bumps configured to enhance grip of the knob.

7. The alignment system of claim 1, wherein the cover and the flow selector device each include a component to enable locking the cover to the flow selector device.

8. The alignment system of claim 1, wherein the cover pivots from the flow selector device between an open and closed position and further wherein the knob nests within the cover when the cover is in the closed position.

9. The alignment system of claim 1, wherein the at least one registering element is a plurality of axial ridges defined by the knob.

10. The alignment system of claim 9, wherein the cover element is at least one recess that receives at least one axial ridge allowing the cover to attain its closed position.

11. An alignment system for accurately setting the flow rate of a flow selector device that selectively fixes the flow rate of a fluid; the system comprising:
- a flow selector device including a fluid inlet, a fluid outlet and a flow rate selection mechanism that is rotated between a plurality of pre-selected positions corresponding to pre-determined flow rates;
- a knob providing a grip to rotate the flow rate selection mechanism, the knob comprising a body having a distal portion, a proximal portion, and further defining a plurality of axial recesses;
- a cover movable between an open position providing access to the knob and a closed position restricting access to the knob, the cover further including at least one prong that: (i) engages the distal portion of the knob in a region between axial recesses defined the knob when one of the axial recesses defined by the knob is misaligned with a pre-selected position preventing the cover from attaining its closed position, and (ii) is received by one of the axial recesses defined by the knob when the knob is aligned with a pre-selected position allowing the cover to attain its closed position,
- wherein the knob is positioned between the flow rate selection mechanism and the cover.

12. The alignment system of claim 11, further comprising a plurality of indicia corresponding to the pre-selected positions and wherein the cover limits visibility to a single indicia when the cover is closed.

13. The alignment system of claim 12, wherein the cover includes a window for viewing the single indicia.

14. The alignment system of claim 11, wherein the knob is detachable, substantially cylindrical and uniform in diameter and the portion of the knob defining the plurality of axial recesses further define bumps configured to enhance grip of the knob.

15. The alignment system of claim 11, wherein the cover and the flow selector device each include a component to enable locking the cover to the flow selector device.

16. The alignment system of claim 11, wherein the cover pivots from the flow selector device between an open and closed position and further wherein the knob nests within the cover when the cover is in the closed position.

17. An alignment system for accurately setting the flow rate of a flow selector device that selectively fixes the flow rate of a fluid; the system comprising:
- a flow selector device including a fluid inlet, a fluid outlet and a flow rate selection mechanism that is rotated between a plurality of pre-selected positions corresponding to pre-determined flow rates;
- a knob providing a grip to rotate the flow rate selection mechanism, the knob comprising a body having a distal portion, a proximal portion, and further defining a plurality of axial ridges;
- a cover movable between an open position providing access to the knob and a closed position restricting access to the knob, the cover further including a plurality of cover recesses such that: (i) the cover engages the distal portion of the knob when one of the axial ridges defined by the knob is misaligned with a pre-selected position preventing the cover from attaining its closed position, and (ii) one of the axial ridges defined by the knob is received by a cover recess when the knob is aligned with a pre-selected position allowing the cover to attain its closed position,
- wherein the knob is positioned between the flow rate selection mechanism and the cover.

18. The alignment system of claim 17, further comprising a plurality of indicia corresponding to the pre-selected positions and wherein the cover limits visibility to a single indicia when the cover is closed.

* * * * *